United States Patent [19]

Chiang

[11] Patent Number: 4,571,429

[45] Date of Patent: Feb. 18, 1986

[54] PROCESS FOR THE PREPARATION OF O-CARBOETHOXYBENZENESULFONA-MIDE

[75] Inventor: George C. Chiang, Wilmington, Del.

[73] Assignee: E. I. Du Pont de Nemours and Company, Wilmington, Del.

[21] Appl. No.: 730,155

[22] Filed: May 3, 1985

[51] Int. Cl.⁴ .......................................... C07C 143/67
[52] U.S. Cl. ....................................................... 560/12
[58] Field of Search .......................... 560/12; 548/211

[56] References Cited

U.S. PATENT DOCUMENTS 2,946,815  7/1960  Hamor .................................. 560/12
3,008,928  11/1961 Rueggeberg ......................... 560/12
3,399,123  8/1968  Passal .................................. 560/12

OTHER PUBLICATIONS

Loev, J. Org. Chem., 27, pp. 1703–1709 (1962).

Primary Examiner—Michael L. Shippen

[57] ABSTRACT

Saccharin is reacted with ethanol and concentrated sulfuric acid. Sodium acetate is used to remove saccharin from the crude material so that highly pure o-carboethoxybenzene sulfonamide is recovered.

4 Claims, No Drawings

PROCESS FOR THE PREPARATION OF O-CARBOETHOXYBENZENESULFONAMIDE

BACKGROUND OF THE INVENTION

This invention relates to intermediate compounds used to prepare herbicides. More particularly, it relates to intermediate compounds used to prepare herbicidal compounds disclosed in U.S. Pat. No. 4,393,506, and U.S. application Ser. No. 392,364, now adandoned.

The *Journal of Organic Chemistry*, 27, pages 1705–1706 (1962) and references cited therein disclose the reaction of saccharin with alcohols in the presence of hydrochloric acid or methanesulfonic acid to give 2-sulfamylbenzoic acid esters. However, no suggestion is set out for the separation of the desirable 2-sulfamylbenzoic acid ester from residual saccharin. One skilled in the organic chemical art might employ a caustic wash to remove the saccharin. However, upon treatment with caustic wash, o-carboxybenzene sulfonamide goes back to saccharin. In fact, during caustic treatment, a stable pH end point cannot be achieved. In addition, an O-ethylsaccharin by-product survives the caustic treatment, leaving the final intermediate product contaminated with several percent of this unwanted by-product.

SUMMARY OF THE INVENTION

A precise chemical recipe has been invented which insures the production in high yield (>80%) of the desired o-carboethoxybenzene sulfonamide intermediate with a high purity (>95%).

Reaction of saccharin SAC with ethanol and sulfuric acid produces an equilibrium mixture of o-carboethoxybenzene sulfonamide I and O-ethylsaccharin OES as shown in the following equation.

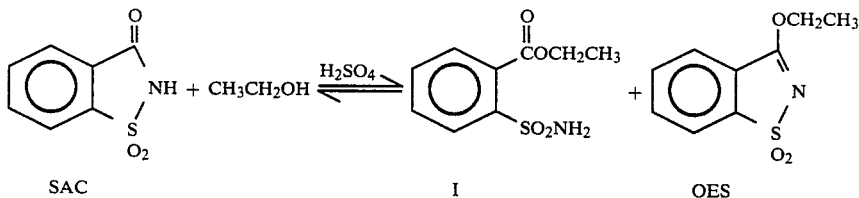

SAC                           I                            OES

The crude product obtained from this reaction through crystallization and filtration also contains unreacted saccharin.

The method of the current invention employs a high loading of concentrated $H_2SO_4$ in the reaction resulting in a low level of OES in the crude product. In addition, this process employs aqueous sodium acetate for the removal of saccharin from the crude material, leading to product of excellent quality. The organic mother liquor is recycled. The process of this invention has been demonstrated successfully with up to nine recycles. Averaged yield of final product was greater than 80%. Purity of final product was greater than 95%.

DETAILED DESCRIPTION OF THE INVENTION

The process of this invention is carried out by reacting one mole of saccharin with 8 to 16 moles of ethanol and 0.10 to 0.82 moles of sulfuric acid. The reaction mixture is refluxed for 2 to 4 hours under a nitrogen atmosphere and then cooled to a temperature of 10° C. to 30° C. with a water bath. The clear reaction solution is seeded with o-carboethoxybenzene sulfonamide to induce crystallization. The crude mixture containing o-carboethoxybenzene sulfonamide, saccharin and O-ethylsaccharin is filtered off and the filtrate is recycled.

The wet filter cake is reslurried with water and the pH is adjusted to 4.5 with sodium acetate. The resulting slurry is filtered to give purified o-carboethoxybenzene sulfonamide.

The following Examples set forth the invention in greater detail.

EXAMPLE 1

To a 2-l 3-necked R.B. flask was charged 183.2 g (1 mole) saccharin, 946 ml (2 pints) absolute alcohol and 40 g conc. $H_2SO_4$. The above reaction mixture was refluxed for 3 hours under a $N_2$ atmosphere and then cooled to ambient temperature (15°–20° C.) with a water bath. Pure seeds (ca. 0.1 g) of o-carboethoxybenzene sulfonamide were introduced to induce crystallization. The clear reaction solution soon turned into a white slurry. After 15 minutes, crude o-carboethoxybenzene sulfonamide was filtered off. The filtrate was to be used in recycle runs (Example 2). The wet filter cake (65.6 g) was reslurried with 1-l of water and the pH adjusted to 4.5 with sodium acetate. The resulting slurry was filtered to give purified product which was washed several times with water and then dried in a vacuum oven at 50° C. The final product was >96% pure with 0–3% of O-ethylsaccharin. It did not contain any detectable saccharin.

EXAMPLE 2

Filtrate from Example 1 was returned to the original 2-l flask. For the recycle run, 140 ml of absolute alcohol, 5.3 g of conc. $H_2SO_4$ and 183.2 g of saccharin were charged. The reaction mixture was refluxed for 2 hours and then cooled to 20° C. Crystallization took place without seeding. The white slurry was filtered to give 216.0 g of crude o-carboethoxybenzene sulfonamide. The filtrate was to be used in the next recycle. The wet cake was slurried in 1-l water and pH was adjusted to 4.5 with sodium acetate. Filtration of the slurry yielded a wet cake which was washed with water, dried in a vacuum oven at 50° C. to yield pure o-carboethoxybenzene sulfonamide. LC assay of the purified product showed >95% content of o-carboethoxybenzene sulfonamide, 0.4–4.8% O-ethylsaccharin and no detectable saccharin. Averaged yield of final product from 9 recycle runs was 83.1%.

What is claimed is:

1. A process for producing o-carboethoxybenzene sulfonamide in high yield and purity comprising reacting saccharin with ethanol and concentrated sulfuric acid to produce a crude crystallized material containing residual saccharin, isolating the crude crystallized material by filtration and retaining the organic filtrate, and thereafter slurrying the crude material in aqueous sodium acetate to remove the saccharin residue therefrom and removing the pure o-carboethoxybenzene sulfonamide by filtration.

2. The process of claim 1 wherein the reaction of saccharin, ethanol and sulfuric acid is carried out under nitrogen atmosphere.

3. The process of claim 1 wherein the crude material is slurried with water and the pH adjusted to 4.5 with sodium acetate.

4. The process according of claim 1 further comprising combining the organic filtrate with saccharin, ethanol and concentrated sulfuric acid, refluxing to produce a crude crystallized material, isolating the crude material by filtration, retaining the organic filtrate, slurrying the crude material with water and adjusting the pH to 4.5 with sodium acetate and removing the purified o-carboethoxybenzene sulfonamide by filtration.

* * * * *